(12) United States Patent
Restaino

(10) Patent No.: US 7,150,977 B2
(45) Date of Patent: Dec. 19, 2006

(54) **PLATING MEDIA FOR THE IDENTIFICATION OF *SALMONELLA***

(75) Inventor: Lawrence Restaino, Elburn, IL (US)

(73) Assignee: R&F Products, Inc., Downers Grove, IL (US)

( * ) Notice: Subject to any disclaimer, the term of this patent is extended or adjusted under 35 U.S.C. 154(b) by 0 days.

(21) Appl. No.: 10/784,347

(22) Filed: Feb. 23, 2004

(65) Prior Publication Data

US 2004/0166557 A1 Aug. 26, 2004

Related U.S. Application Data

(63) Continuation-in-part of application No. 09/885,204, filed on Aug. 20, 2001, now abandoned.

(51) Int. Cl.
*C12Q 1/10* (2006.01)
*C12Q 1/04* (2006.01)
*C12Q 1/54* (2006.01)
*C12Q 1/34* (2006.01)

(52) U.S. Cl. ............................ 435/38; 435/34; 435/14; 435/18

(58) Field of Classification Search .................. 435/14, 435/18, 34, 38, 7.35, 7.72
See application file for complete search history.

(56) References Cited

U.S. PATENT DOCUMENTS 5,434,056 A * 7/1995 Monget et al. ............... 435/14
5,726,031 A * 3/1998 Roth et al. .................... 435/34

* cited by examiner

*Primary Examiner*—Robert A. Wax
*Assistant Examiner*—Rosanne Kosson
(74) *Attorney, Agent, or Firm*—Marshall A. Burmeister

(57) ABSTRACT

An isolation plating medium for the identification of *Salmonella* bacteria in a sample containing a plurality of different bacteria comprising a mixture of a carbohydrate capable of being a metabolic source for *Salmonella* bacteria and supporting colonies of *Salmonella* bacteria, a pH indicator dye that changes the color of the plating medium to a first color different from the color of the medium responsive to a change in the pH of the medium, a first substrate that does not react with *Salmonella* bacteria and injects color into the medium of a second color responsive to the presence of beta-galactosidase, the second color contrasting with the first color and the color of the medium, a second substrate that does not react with *Salmonella* bacteria and injects color into the medium of substantially the same color as the second color responsive to the presence of beta=galactosidase, and an ingredient for thickening the mixture in sufficient quantity to solidify the mixture.

12 Claims, No Drawings

PLATING MEDIA FOR THE IDENTIFICATION OF SALMONELLA

This application is a continuation-in-part of application Ser. No. 09/885,204, filed Aug. 20, 2001 now abandoned. The present invention relates to isolating plating media enabling the presumptive identification of *Salmonella* bacteria, and to methods of differentiating *Salmonella* bacteria from other bacteria in a plating medium.

BACKGROUND OF THE INVENTION

*Salmonella* is pathogenic for man, and the identification of *Salmonella* bacteria is a significant problem in medical bacteriology and in monitoring foodstuffs. It is of particular concern in the poultry and egg industries.

There have been many efforts to develop a selective plating medium for identifying *Salmonella* bacteria in samples containing mixed bacteria. "The Compendium of Methods for the Microbiological Examination of Foods" published by the American Public Health Association, 1992, describes some of these prior art processes at pages 382–383. In general, the prior art plating media for identifying *Salmonella* bacteria in a sample of mixed bacteria lack specificity, are difficult to read, and are subject to false positives and/or false negatives. Further, many of the plating media of the prior art provide nutrients that are more advantageous for strains of bacteria other than *Salmonella*, hence providing a faulty indication of the presence of *Salmonella*. As a result there has been a continuing effort to develop a plating medium for identifying *Salmonella* in a mixed sample that overcomes or reduces the deficiencies of such media of the prior art.

The prior art includes U.S. Pat. No. 4,279,995, dated Jul. 21, 1981, to Woods et al. entitled "Selective *Salmonella* Carbohydrate and Medium Constructed Therefrom" which discloses a plating medium with 2-Deoxy-D-Ribose as a selective carbohydrate for *Salmonella* and a pH indicator dye to respond to carbohydrate metabolism. The media allows the growth of *Salmonella* spp., *Arizona* spp. to the exclusion of other *Enterobacteriaceae*, but it also permits the growth of *Citrobacter freundii*.

U.S. Pat. No. 5,098,832 dated Mar. 24, 1992, and divisional U.S. Pat. No. 5,194,374 to Rambach entitled "Isolating Medium for Identifying the *Salmonella* Bacterium" disclose a plating medium with 1,2-propanediol/silica gel that is metabolizable by *Salmonella* and a pH indicator to react to acidification of the medium. These patents also disclose the addition of a beta-galactosidase chromogenic substrate to increase the specificity of the medium.

U.S. Pat. No. 5,434,056 dated Jul. 18, 1995, to Monget et al., entitled "Method of Bacteriological Analysis, and Medium for the Detection of Bacteria of the *Salmonella* Genus," discloses a plating medium in which the acidic fermentation of sodium glucuronate monitored with a pH indicator, and a beta-D-galactopyraniside chromogenic substrate are used to facilitate selection of *Salmonella* colonies.

U.S. Pat. No. 5,786,167 dated Jul. 28, 1998, to Tuompo, et al., entitled "Method and Culture Medium for Identification of *Salmonella*," discloses a plating medium in which the acidic fermentation of melibiose, mannitol, and sorbitol is monitored with a pH indicator, and a beta-galactosidase responsive chromogenic substrate is used to facilitate selection of *Salmonella* colonies.

U.S. Pat. No. 5,871,944 dated Feb. 16, 1999 to Miller et al. entitled "*Salmonella* Preferential Media" discloses a plating medium containing lactose and cellobiose as the carbohydrate source. In one embodiment, the production of $H_2S$ is used to indicate *Salmonella*. In another embodiment, 5-bromo-4-chloro-3-indolyl-beta-D-galactopyranoside is incorporated in the medium and this chromogenic substrate is used to provide a color change to indicate bacteria other than *Salmonella*.

As indicated by the prior art set forth above, there continues to be a need for a plating medium for the differentiation of *Salmonella* that is more specific, easier to read, produces fewer false positives or false negatives, and is more sensitive to *Salmonella* bacteria.

SUMMARY OF THE INVENTION

The 1981 U.S. Pat. No. 4,279,995 of Woods and Wilkinson, supra, discloses the process of selectively differentiating *Salmonella* spp., *Arizona* spp. and some of the *Citrobacter freundii* from other members of the *Enterobacteriaceae* by using a medium containing 2-deoxy-D-ribose as a carbohydrate source and monitoring the metabolic acid of the medium. This patent further teaches the use of inhibitors to reduce or eliminate response of the medium to *Citrobacter freundii* and other non-target bacteria, but inhibitors also tend to have an adverse effect on the growth of target bacteria, particularly some strains of *Salmonella*. In accordance with the present invention, at least two chromogenic substrates are added to the differentiating medium to color colonies of non-target bacteria with essentially the same distinctive color, a color that contrasts with both the medium and the color produced by detection of the metabolic activity of *Salmonella* bacteria in the medium.

A plurality of chromogenic substrates is desirable to differentiate a sample containing a mixture of members of the *Enterobacteriaceae* because a positive reaction between the substrate and non-target bacteria is necessary, and chromogenic substrates are generally selective. For example, *Citrobacter* does not react with beta-glucuronapyronaside but is reported to be 93% positive to beta-galactopyronoside. Hence, the present invention, in its preferred embodiment, utilizes beta-galactopyranoside substrates and effectively eliminates a response from *Citrobacter* which takes the color of the substrate.

There is also another advantage to incorporating multiple substrates in a plating media, and that is improved readability. Some substrates react more quickly to a particular enzyme than other substrates, and the fast acting substrates tend to wash out after a period of time making it more difficult to identify target cells against the background color of the medium. This is particularly true of a medium which also contains a carbohydrate and an indicator dye. By also incorporating a second substrate that produces the same color precipitate as the first substrate, but does so more slowly than the first substrate, the target colonies will maintain their color contrast with the background color of the medium, and the target cells will be easier to read. In the preferred embodiment of the present invention, the plating media contains both 5-bromo-4-chloro-3-indoxyl-β-D-galactopyranoside (X-Gal) and 3-indoxyl-β-D-galactopyranoside (Y-Gal). Both substrates react to the galactosidase enzyme to produce blue-black colonies in the substrate, but the X-Gal substrate produces an immediate blue-black colony that then fades, and the Y-Gal substrate produces colonies of the same blue-black color but at a slower rate and with a more intense color. Hence, by incorporating both an X-Gal substrate and a Y-Gal substrate in the plating medium the presence of a target colony will be more distinct, even if the medium also includes a carbohydrate and indicator dye which effect the color of the medium, as in the present invention.

Many of the bacteria that are found in mixed samples can be removed from the differentiation process by inhibitors without adversely effecting growth of *Salmonella* bacteria, particularly bacteria that are not members of the *Enterobacteriaceae*. Accordingly, a preferred embodiment of plating medium according to the present invention contains inhibitors.

DETAILED DESCRIPTION OF THE INVENTION

The selection of the carbohydrate, and the substrates determines the selectivity of a plating medium according to the present invention. A plating medium for differentiation of *Salmonella* bacteria, according to the present invention, can use most carbohydrates that produce metabolic reactions with *Salmonella*, but preferably the carbohydrate will not react with other bacteria, particularly other members of the family *Enterobacteriacese*. 2-Deoxy-D-Ribose, xylose, mannitol, dulcitol, sorbitol, L-rhamnose and D-arabitol have been found to be suitable, and of this group of carbohydrates, 2-Deoxy-D-Ribose is preferred because of its strong positive reaction with *Salmonella* bacteria, including *Salmonella typhi*, and very few other bacteria of the *Enterobacteriacese*.

The selection of the substrates depends upon the carbohydrate and indicator dye selected, since it will be the function of the substrates to change the color of colonies of non-target bacteria to a common color that contrasts with the color of the dye and may be substantially ignored when assaying *Salmonella* colonies. The substrate may be either chromogenic or fluorogenic, and it is intended that the term substrate include both forms of substrates. The preferred substrates for differentiation of *Salmonella* are 5-bromo-4-chloro-3-indoxyl-beta-D-galactopyraniside, 5-bromo-6-chloro-3-indoxyl-beta-D-galactopyraniside, 3-indoxyl-beta-D-galactopyraniside, 6-chloro-3-indoxyl-beta-D-galactopyraniside, 4-nitrophenyl-beta-D-galactopyranoside, 2-nitrophenyl-beta-D-galactopyranoside, 5-iodo-3-indoxyl-beta-D-galactopyranoside, 4-methylumbelliferyl-beta-D-galactopyraniside and N-methylindoxyl-beta-D-galactopyranoside, but other substrates that do not react with *Salmonella* bacteria and do react with non-target bacteria may also be used. The substrates should be selected to produce water insoluble precipitate of approximately the same color from non-target bacteria.

It is also desirable to increase the production of precipitate from the chromogenic substrates by including an enhancer in the medium. The preferred embodiment of a plating medium according to the present invention includes the enhancer isopropyl-beta-D-thiogalactopyranoside. Other suitable enhancers are 1-O-methyl-beta-D-galactopyranoside, ethyl-beta-D-thiogalactopyranoside, and methyl-beta-D-thiogalactopyranoside.

A pH indicator dye is required to produce *Salmonella* colonies of a contrasting color with the colonies of non-target bacteria. In the preferred embodiment of the invention, the non-target bacteria produce colonies of deep blue or purple, and a suitable pH indicator dye that will contrast with the deep blue may be red. Accordingly, the preferred embodiment incorporates a neutral red indicator dye. It is to be understood that other dyes may be used, provided the dye contrasts with the color produced by the chromogenic substrates and with the color of the medium.

A number of inhibitors are desirable in the plating media of the present invention. One group of organisms that may readily be inhibited is gram-positive bacteria which are inhibited by bile salt and bile salt #3. Other inhibitors that may be used in the media of this invention are tellurite to retard the growth of *Escherichia*, sodium novobiocin to inhibit *Proteus* sp. and cefsulodin to inhibit *Pseudomonas/Aeremonas* sp.

The following table sets forth the ingredients of a plating medium that constitutes the preferred embodiment of the present invention.

TABLE 1

| Chemical | Grams/liter |
|---|---|
| Yeast Extract | 3.00 |
| Proteose Peptone | 10.00 |
| Lab Lemco Powder | 1.00 |
| Sodium Chloride | 5.00 |
| L-Phenylalanine | 3.50 |
| Ferric Ammonium Citrate | 0.50 |
| Bile Salts #3 | 0.40 |
| Bile Salts | 0.20 |
| 5-bromo-4-chloro-3-indoxyl-beta-D-galactopyraniside | 0.15 |
| 3-indoxyl-beta-D-galactopyraniside | 0.15 |
| Isopropyl-beta-D-thiogalactopyranoside | 0.10 |
| Neutral red | 0.03 |
| Agar | 15.97 |
| Deionized Water | 950 ml/l. |
| Supplements | |
| 2-Deoxy-D-Ribose | 12.00 |
| Sodium novobiocinocin | 0.02 |
| Cefsulodin | 0.006 |

When preparing the medium, the ingredients, excepting the supplements, are mixed together in any order and thereafter boiled and cooled to form a basal medium. Thereafter, the supplements are added to the cooled, boiled basal medium just prior to completion of the plating medium.

Table 2 sets forth the results of tests made with a medium according to the preferred embodiment of the invention, as set forth in Table 1 above. The bacterial strains were incubated on the medium of Table 1 for 24 hours at 35 degrees Celsius, and Table 2 reports the results.

TABLE 2

| Bacterial Strains | # of Strains | Colonial Morphology |
|---|---|---|
| *Salmonella* spp. (non *S. typhi*) | 40 | Raised colony; 1.5–4.0 mm in diameter-, Reddish pink color. Some strains may have a pink precipitate surrounding the colony or a clear to light pink ring around the colony. |
| *Salmonella typhi* | 1 | Raised colony; 1.0–1.5 mm in diameter. Reddish pink color with no precipitate surrounding the colony Clear to light pink ring around the colony. |
| *Salmonella tennessee* | 1 | Raised colony; 2.0–3.0 mm in diameter. Dark blue color with a pink precipitate and no clear ring around the colony. |
| *Escherichia coli* 0157: H7 | 10 | Domed to raised colony; 1.0–3.0 mm in Diameter, Bluish green color with bluish green precipitate. no clear ring around the colony. |
| *Escherichia coli* | 9 | Domed to raised colony; 2.0–4.0 mm in Diameter. |

TABLE 2-continued

| Bacterial Strains | # of Strains | Colonial Morphology |
|---|---|---|
| Escherichia coli | 4 | Bluish green color with bluish green precipitate. No clear ring around the colony. Domed to raised colony; 2.0–3.0 mm in Diameter. |
| Escherichia coli | 1 | Dark blue in color with a pink precipitate. No clear ring around the colony. Raised colony; 2.0 mm in diameter.. Reddish pink color with a pink precipitate. Thin clear ring around the colony. |
| Escherichia hermannii | 2 | Domed colony; Pinpoint to 1.0 mm in Diameter. Clear to greenish blue with no precipitate and ring around the colony. |
| Citrobacter diversus | 1 | Domed to raised; Pinpoint to 1 mm in Diameter. Greenish blue color with no precipitate. |
| Citrobacter freundii | 2 | Domed colony; 2.0–3.0 mm in diameter Dark blue to bluish green in color with no Precipitate and ring around the colony. |
| Serratia marcesceens | 1 | Domed colony; 2.0 mm in diameter. Light green in color with no precipitate. Thick clear ring around the colony. |
| Hafnia alvei | 4 | Domed colony; Pinpoint to 1.0 mm in diameter. Bluish green in color with bluish green precipitate; no ring around the colony |
| Enterobacter agglomerans | 4 | Domed colony; 1.0–3.0 mm in diameter. |
| Enterobacter cloacae | | Bluish green in color with no |
| Enterobacter aerogenes | | Precipitate. |
| Enterobacter sakazakii | | With or without a clear thin ring around the colony. |
| Klebslella ozaenae | 1 | Domed colony; 1.0–2.0 mm in diameter. Clear to tan in color with no precipitate. |
| Klebsiella pneumoniae | 2 | Domed colony; 2.0–3.0 mm in diameter. Bluish green in color with bluish precipitate arid no clear ring around the colony. |
| Morganella morganii | 1 | Domed colony; 1.0–2.0 mm in diameter. Clear to cream color with a brownish precipitate in the medium. No clear ring around the colony. |
| Providencia retigeri | 3 | Domed colony; Pinpoint to 2.0 mm iii diameter. |
| Providencia alealifaeiens | | |
| Providencia stuartii | | Clear to tan color with brownish Precipitate in the medium. No clear ring around the colony. |
| Acineobacter calcouceticus | 8 | No growth for all strains tested. |
| Proteus mirabillis | | |
| Pseudomonas aeruginosa | | |
| Yersenia enterocolitica | | |
| Pseudomonas pickettii | | |
| Aeromonas hydrophila | | |

From Table 2, it is clear that the medium of the present invention is highly selective for *Salmonella* spp. and *Salmonella typhi* bacteria, and that samples containing mixed bacteria on plates of that medium that have been properly incubated are readily assayed because the target colonies are uniquely colored. The use of a carbohydrate and a pH indicator dye to color colonies of the target bacteria and multiple chromogenic substrates to color colonies of non-target bacteria has provided improved selectivity and facilitated assaying. *Salmonella* bacteria are positive with respect to the selected carbohydrate, and negative with respect to the substrates, thus forming colonies with the color of the dye. Non-target bacteria that are negative with respect to the carbohydrate and positive with respect to one or both substrates produce colonies with the color of the precipitate of the substrate. If the non-target bacteria are also positive with respect to the carbohydrate, colonies of these bacteria will assume a color that is a blend of the color of the dye and the active substrate or substrates.

While the plates of the preferred embodiment of this invention are designed for the identification of *Salmonella* bacteria, those skilled in the art will be able to adapt this invention readily for the identification of other microorganisms. It is therefore intended that the scope of this invention be not limited by the specification, but rather only by the appended claims.

The invention claimed is:

1. A differential plating medium for the detection of *Salmonella* bacteria from a sample likely to contain *Salmonella* bacteria and other bacteria, said other bacteria releasing the enzyme beta-galactosidase on exposure to a substrate in the plating medium, comprising a mixture of (1) a carbohydrate that is a metabolic source for *Salmonella* bacteria, the metabolic reaction between *Salmonella* bacteria and the carbohydrate releasing acid into a portion of the medium of the reaction, (2) a pH indicator dye that changes the color of said portion of the plating medium to a first color different from the color of the medium responsive to a change in the pH of said portion of the medium, (3) a first substrate that does not react with *Salmonella* bacteria but reacts with the enzyme beta-galactosidase to produce a second color in the medium where it is acted upon by the enzyme beta-galactosidase, the second color contrasting with the first color and the color of the medium, (4) a second substrate that does not react with *Salmonella* bacteria but reacts with the enzyme beta-galactosidase to produce said second color in the medium where it is acted upon by the enzyme beta-galactosidase of, the first substrate reacting with the enzyme beta-galactosidase in a significantly shorter time than the second substrate, whereby colonies of said other bacteria contain the second color, and (5) an ingredient for thickening the mixture in sufficient quantity to solidify the mixture, wherein the first substrate and the second substrate are selected from the group consisting of 5-bromo-4-chloro-3-indoxyl-beta-D-galactopyranoside, 5-bromo-6-chloro-3-indoxyl-beta-D-galactopyranoside, 3-indoxyl-beta-D-galactopyranoside, 6-chloro-3-indoxyl-beta-D-galactopyranoside, 4-nitrophenyl-beta-D-galactopyranoside, 2-nitrophenyl-beta-D-galactopyranoside, 5-iodo-3-indoxyl-beta-D-galactopyranoside, 4-methylumbelliferyl-beta-D-galactopyranoside and N-methylindoxyl-beta-D-galactopyranoside.

2. A differential plating medium for the detection of *Salmonella* bacteria from a sample likely to contain *Salmonella* bacteria and other bacteria comprising the medium of claim 1, wherein the carbohydrate is one or more members of the group consisting of 2-deoxy-D-ribose, xylose, mannitol, dulcitol, sorbitol, L-rhamnose and D-arabitol.

3. A differential plating medium for the detection of *Salmonella* bacteria from a sample likely to contain *Salmonella* bacteria and other bacteria comprising the medium of claim 1, wherein the first substrate is 5-bromo-4-chloro-3-indoxyl-beta-D-galactopyranoside, and the second substrate is 3-indoxyl-beta-D-galactopyranoside.

4. A differential plating medium for the detection of *Salmonella* bacteria from a sample likely to contain *Salmo-*

*nella* bacteria and other bacteria comprising the medium of claim 2 in combination with an inhibitor selected from the group consisting of bile salt, bile salt #3, tellurite, sodium novobiocin and cefsulodin.

5. A differential plating medium for the detection of *Salmonella* bacteria from a sample likely to contain *Salmonella* bacteria and other bacteria comprising the medium of claim 1 in combination with a chromogenic substrate enhancer.

6. A differential plating medium for the detection of *Salmonella* bacteria from a sample likely to contain *Salmonella* bacteria and other bacteria comprising the medium of claim 5, wherein the chromogenic substrate enhancer consists of at least one member of the group consisting of isopropyl-beta-D-thiogalactopyranoside, 1-o-methyl-beta-D-galactopyranoside, methyl-beta-D-thiogalactopyranoside, and methyl-beta-D-thiogalactopyranoside.

7. A differential plating medium for the detection of *Salmonella* bacteria from a sample likely to contain *Salmonella* bacteria and other bacteria comprising the medium of claim 1, wherein the carbohydrate is 2-deoxy-D-ribose and the first and second chromogenic substrates are 5-bromo-4-chloro-3-indoxyl-beta-D-galactopyranoside and 3-indoxyl-beta-D-galactopyranoside, respectively.

8. A differential plating medium for the detection of *Salmonella* from a sample containing *Salmonella* and a plurality of other bacteria that release the enzyme beta-galactosidase upon exposure to a mixture consisting essentially of (1) at least one carbohydrate that is metabolizable by *Salmonella* and is of the group consisting of 2-deoxy-D-ribose, xylose, mannitol, dulcitol, sorbitol, L-rhamnose and D-arabitol, the metabolic reaction between the carbohydrate and *Salmonella* bacteria releasing acid into a portion of the medium of the reaction, (2) a pH indicator dye that changes the color of said portion of the plating medium to a first color responsive to a change in the pH of the medium, (3) a first chromogenic substrate that does not react with *Salmonella* bacteria and changes the color of the medium to a second color responsive to the presence of the beta-galactosidase enzyme, (4) a second chromogenic substrate that does not react with *Salmonella* bacteria and that changes the color of the medium to approximately the same second color, and that is responsive to the presence of the beta-galactosidase enzyme, the first substrate reacting with the beta-galactosidase enzyme more quickly than the second substrate, and the first and second colors contrasting with each other and with the color of the medium, wherein the first substrate and the second substrate are selected from the group consisting of 5-bromo-4-chloro-3-indoxyl-beta-D-galactopyranoside, 5-bromo-6-chloro-3-indoxyl-beta-D-galactopyranoside, 3-indoxyl-beta-D-galactopyranoside, 6-chloro-3-indoxyl-beta-D-galactopyranoside, 4-nitrophenyl-beta-D-galactopyranoside, 2-nitrophenyl-beta-D-galactopyranoside, 5-iodo-3-indoxyl-beta-D-galactopyranoside, 4-methylumbelliferyl-beta-D-galactopyranoside and N-methylindoxyl-beta-D-galactopyranoside, and (5) an ingredient for thickening the mixture in sufficient quantity to solidify the mixture.

9. A differential plating medium for the detection of *Salmonella* bacteria from a sample likely to contain *Salmonella* bacteria and other bacteria comprising the medium of claim 8, wherein the ingredient for thickening the mixture is agar.

10. A method of detecting the presence of *Salmonella* in a sample that is likely to contain *Salmonella* bacteria and other bacteria, comprising the steps of inoculating the plating medium of claim 1 with the sample, thereafter incubating said plating medium for a sufficient period to obtain colonies of bacteria producing one or more of said colors, and examining the plating medium for colonies of said first color.

11. The method of claim 10, wherein the carbohydrate is one or more members of the group consisting of 2-deoxy-D-Ribose, xylose, mannitol, dulcitol, sorbitol, L-rhamnose and D-arabitol.

12. The method of claim 10, wherein the plating medium further comprises a chromogenic substrate enhancer.

\* \* \* \* \*

UNITED STATES PATENT AND TRADEMARK OFFICE
CERTIFICATE OF CORRECTION

PATENT NO. : 7,150,977 B2
APPLICATION NO. : 10/784347
DATED : December 19, 2006
INVENTOR(S) : Lawrence Restaino It is certified that error appears in the above-identified patent and that said Letters Patent is hereby corrected as shown below:

Column 6, line 38, after "beta-galactosidase" delete "of".

Signed and Sealed this

Twenty-seventh Day of February, 2007

JON W. DUDAS
*Director of the United States Patent and Trademark Office*